United States Patent
Brostrom et al.

(10) Patent No.: US 7,283,878 B2
(45) Date of Patent: Oct. 16, 2007

(54) LEAD STABILIZER AND EXTENSION WIRE

(75) Inventors: Thomas D. Brostrom, Blaine, MN (US); Ryan T. Bauer, Plymouth, MN (US); Douglas S. Hine, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 255 days.

(21) Appl. No.: 10/963,184

(22) Filed: Oct. 12, 2004

(65) Prior Publication Data

US 2006/0079949 A1 Apr. 13, 2006

(51) Int. Cl.
*A61N 1/05* (2006.01)

(52) U.S. Cl. .................. 607/119; 607/115; 607/116; 607/122

(58) Field of Classification Search .............. 607/116, 607/119, 115, 122
See application file for complete search history.

(56) References Cited

U.S. PATENT DOCUMENTS

| | | | | |
|---|---|---|---|---|
| 4,488,561 A | * | 12/1984 | Doring | 607/125 |
| 4,846,193 A | * | 7/1989 | Tremulis et al. | 600/585 |
| 5,003,990 A | | 4/1991 | Osypka | 128/772 |
| 5,113,872 A | | 5/1992 | Jahrmarkt et al. | 128/772 |
| 5,246,014 A | | 9/1993 | Williams et al. | 607/122 |
| 5,304,218 A | | 4/1994 | Alferness | 607/122 |
| 5,421,348 A | | 6/1995 | Larnard | 128/772 |
| 5,728,148 A | | 3/1998 | Boström et al. | 607/116 |
| 5,830,157 A | | 11/1998 | Foote | 600/585 |
| 5,873,835 A | | 2/1999 | Hastings et al. | 600/488 |
| 5,897,584 A | | 4/1999 | Herman | 607/122 |
| 5,902,331 A | | 5/1999 | Bonner et al. | 607/122 |
| 5,935,160 A | | 8/1999 | Auricchio et al. | 607/122 |
| 5,999,858 A | | 12/1999 | Sommer et al. | 607/122 |
| 6,132,456 A | | 10/2000 | Sommer et al. | 607/127 |
| 6,185,464 B1 | | 2/2001 | Bonner et al. | 607/119 |
| 6,280,433 B1 | | 8/2001 | McIvor et al. | 604/524 |
| 6,356,791 B1 | | 3/2002 | Westlund et al. | 607/115 |
| 6,379,346 B1 | | 4/2002 | McIvor et al. | 604/524 |
| 6,408,214 B1 | | 6/2002 | Williams et al. | 607/122 |
| 6,625,496 B1 | | 9/2003 | Ollivier | 607/122 |
| 6,671,560 B2 | | 12/2003 | Westlund et al. | 607/116 |
| 2004/0064172 A1 | | 4/2004 | McVenes et al. | 607/122 |
| 2004/0215298 A1 | * | 10/2004 | Richardson et al. | 607/115 |

FOREIGN PATENT DOCUMENTS

EP 1 155 710 A1 11/2001

* cited by examiner

*Primary Examiner*—Carl Layno
*Assistant Examiner*—Shevon E Johnson
(74) *Attorney, Agent, or Firm*—Michael C. Soldner; Steve W. Bauer; Carol F. Barry

(57) ABSTRACT

A lead stabilization and extension wire that enables the withdrawal of a guide catheter over an electrical medical lead body without dislodging an electrode or sensor from an implantation site or detaching the fixation mechanism and methods of use and a kit are disclosed. The lead stabilizer and retraction wire comprises a wire sheath and an elongated core wire insertable within a sheath lumen. The sheath is insertable within a lead body lumen and includes a movable lead clamp that can engage with a lead connector element and a friction element frictionally engaging the core wire to maintain the extension wire length. The lead stabilizer and retraction wire is insertable into the lead body lumen enabling retraction of the guide catheter over the lead stabilization and extension wire while force is applied through the lead stabilization and extension wire to maintain the distal electrode at the implantation site.

28 Claims, 8 Drawing Sheets

140

110

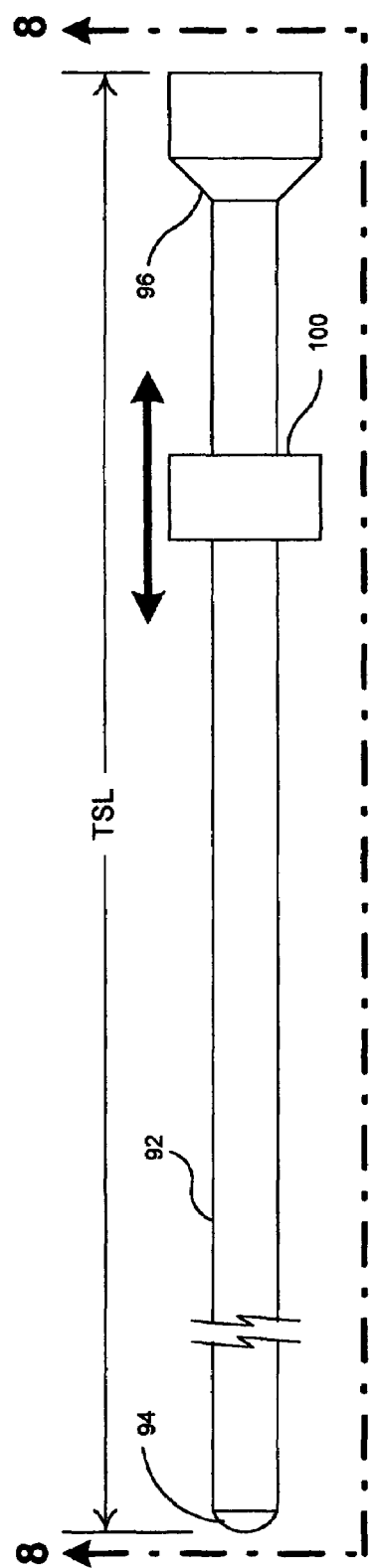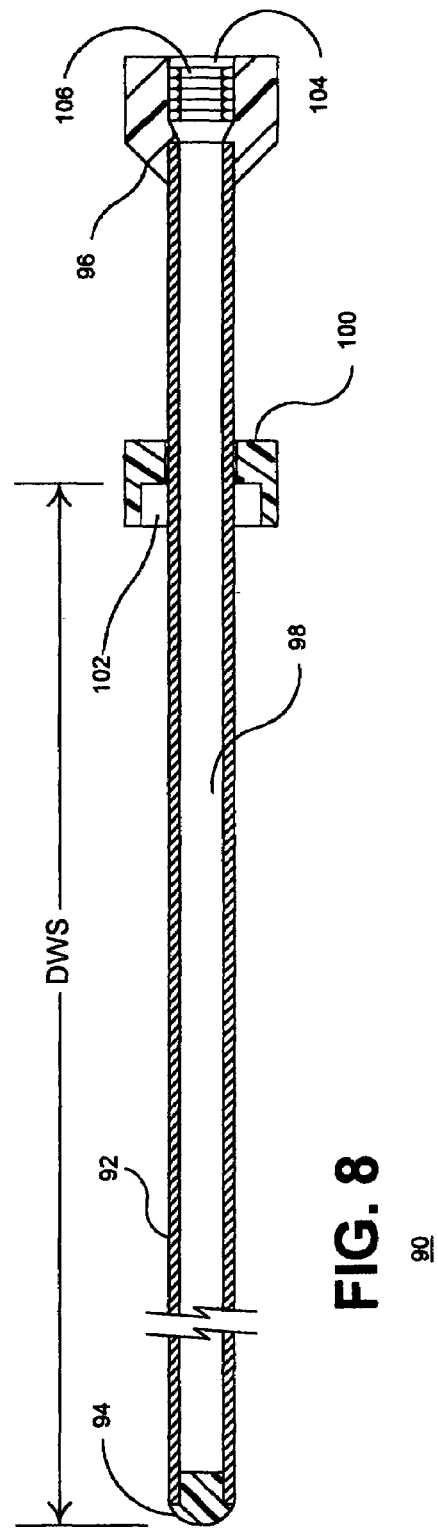
FIG. 7
FIG. 8

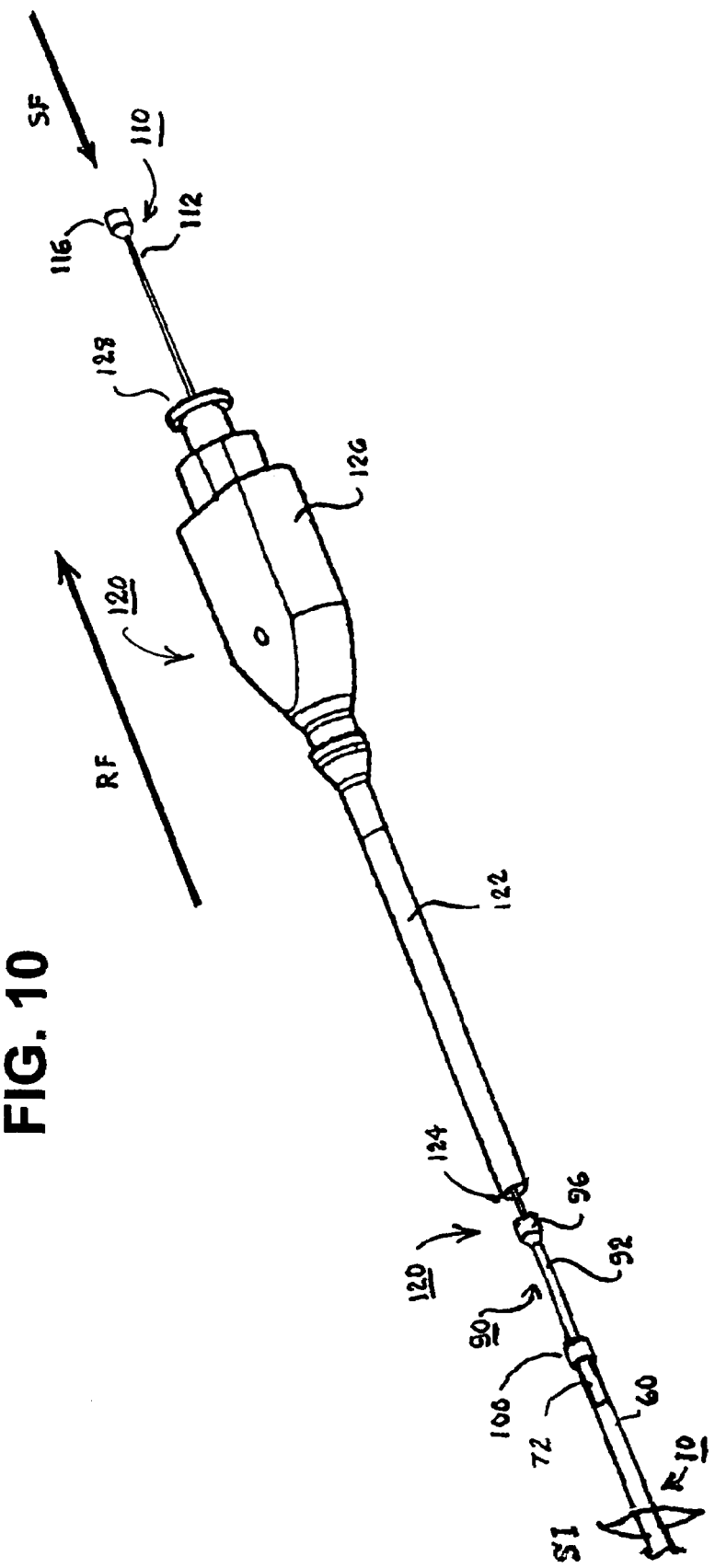

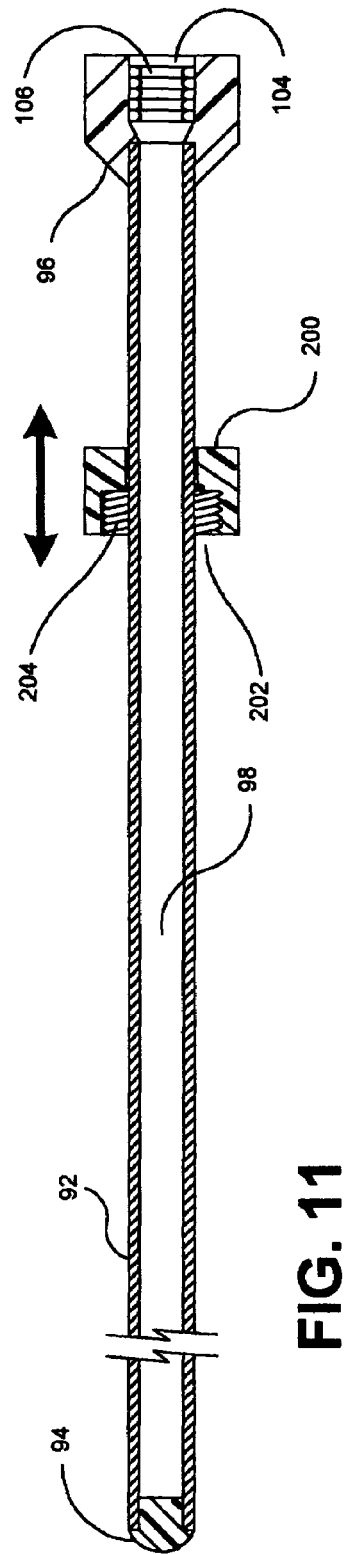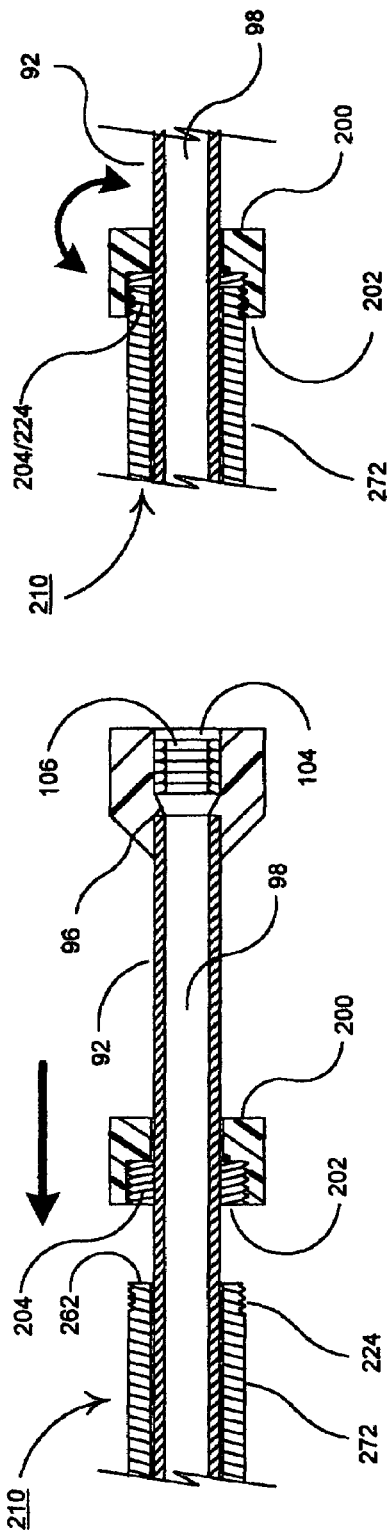

LEAD STABILIZER AND EXTENSION WIRE

TECHNICAL FIELD

The present invention relates to devices and methods employed in the advancement of electrical medical lead through tortuous pathways to dispose one or more electrode or sensor at an implantation site and affix a distal fixation mechanism (if provided on the lead body), and particularly to an implantation kit and method incorporating a lead stabilizer and extension wire that enables the withdrawal of a guide catheter over an electrical medical lead body without dislodging the electrode or sensor from the implantation site or detaching the fixation mechanism.

BACKGROUND

Implantable medical electrical stimulation and/or sensing leads (electrical medical leads) are well known in the fields of tissue stimulation and monitoring, including cardiac pacing and cardioversion/defibrillation, and in other fields of electrical stimulation or monitoring of electrical signals or other physiologic parameters. In the field of cardiac stimulation and monitoring, the electrodes of epicardial or endocardial cardiac leads are affixed against the epicardium or endocardium, respectively, or inserted therethrough into the underlying myocardium of the heart wall.

The lead body of a cardiac lead typically comprises one or more insulated conductive wire surrounded by an insulating outer sheath. Each conductive wire couples a proximal lead connector element with a distal stimulation and/or sensing electrode. The proximal lead connector elements of permanently implantable epicardial and endocardial cardiac leads are designed to be coupled to a pacemaker or defibrillator implantable pulse generator (IPG) or an implanted monitor and to be chronically implanted in the patient's body.

Cardiac leads having a single stimulation and/or sensing electrode at the lead distal end, a single conductor, and a single connector element are referred to as unipolar cardiac leads. Cardiac leads having two or more stimulation and/or sensing electrodes at the lead distal end, two or more respective conductors, and two or more respective connector elements are referred to as bipolar lead or multi-polar leads, respectively.

Epicardial or myocardial cardiac leads, or simply epicardial leads, are implanted by exposure of the epicardium of the heart typically through a limited thorocotomy or a more extensive surgical exposure made to perform other corrective procedures. Endocardial cardiac leads, or simply endocardial leads, are implanted through a transvenous route to locate one or more sensing and/or stimulation electrode along or at the distal end of the lead in a desired implantation site in a chamber of the heart or a blood vessel of the heart. It is necessary to accurately position the electrode surface against the endocardium or within the myocardium or coronary vessel at the implantation site. An active or passive fixation mechanism is typically incorporated into the distal end of permanent cardiac leads and is deployed at the implantation site to maintain the distal end electrode in contact with the endocardium or within the myocardium. Commonly employed active fixation mechanisms comprise a distal fixation helix that is rotated to be screwed into the myocardium and that may function as apace/sense electrode. Commonly employed passive fixation mechanisms comprise a plurality of soft pliant tines that lodge in trabeculae or against a coronary vessel wall or a particularly shaped distal segment of the lead body, e.g., that disclosed in commonly assigned U.S. Pat. No. 5,999,858, that causes the distal pace/sense electrode(s) to bear against a heart chamber wall or coronary vessel wall.

The heart beats approximately 100,000 times per day or over 30 million times a year, and each beat stresses at least the distal end segment of an implanted permanent endocardial lead. The lead conductors and insulation are subjected to cumulative mechanical stresses, as well as material reactions, over the years of implantation that can result in degradation of the insulation or fractures of the lead conductors with untoward effects on device performance and patient well being. The endocardial lead body is subjected to continuous flexing as the heart contracts and relaxes and is formed to be highly supple, flexible and durable. Over the last 30 years, it has become possible to reduce endocardial lead body diameters from 10 to 12 French (3.3 to 4.0 mm) down to 2 French (0.66 mm) presently through a variety of improvements in conductor and insulator materials and manufacturing techniques.

Such a small diameter endocardial lead body lacks the column stiffness necessary to push it through the twists and turns of the venous pathway or vasculature into the right atrium and then to the desired implantation sites in a right heart chamber or within the coronary sinus or a branching cardiac vein. Historically, it has been necessary to temporarily stiffen the lead body to advance the lead distal end through the transvenous pathway and to locate the distal electrode(s) at the desired implantation site either by use of stiffening stylet inserted into a lead body lumen or by advancing the lead body through the lumen of a guide catheter or over a guidewire advanced to the site, or both. Stiffening stylets are typically formed as a single elongated wire in which a distal curve can be manually formed by the implanting physician to induce a like bend in the lead body to facilitate navigation through the vasculature and to aim the distal electrode and/or fixation mechanism against the endocardium or into a coronary vessel. Other stiffening stylets include a handle and pull wire enabling selective changes in curvature of a stylet distal segment while the stylet wire is within the lead body lumen to facilitate such navigation. Certain stiffening stylets comprise an stylet sheath and stylet wire that is movable axially within the stylet sheath, so that the curved distal segment of the stylet wire can be selectively advanced from or retracted into the stylet sheath to facilitate such navigation as disclosed in U.S. Pat. No. 5,728,148, for example.

Various guide catheters typically comprising a guide catheter hub and an elongated guide catheter body have also been proposed for introducing an endocardial lead into the coronary sinus to dispose one or more electrode at an implantation site in the coronary sinus or a branching vessel. Simple single lumen or relatively more complex guide catheters used in certain instances with a stiffening stylet or guidewire are disclosed in commonly assigned U.S. Pat. Nos. 5,246,014, 5,897,584, 6,280,433, 6,379,346 and, 6,408,214, for example. In at least certain embodiments, the guide catheter body is formed to be manually separable or slittable along its length by a slitting tool to aid in removing the guide catheter from the endocardial lead body introduced through a guide catheter lumen after the electrode(s) is disposed at the desired implantation site, and any fixation mechanism is affixed.

A still further technique of implantation of such miniaturized, highly flexible, endocardial leads employs a guidewire that is first advanced through the tortuous transvenous pathway. The endocardial lead is then advanced through the pathway alongside or over the guidewire as disclosed in U.S. Pat. Nos. 5,003,990, 5,304,218, 5,902,331, 6,132,456, and 6,185,464, for example. Some of these techniques require that the lead body be configured to provide an over-the-wire connection and possess sufficient column strength to be advanced over the guidewire. For example, a lead body lumen extends from a proximal lumen opening to a distal lumen opening, and the guidewire is inserted through the lead body lumen to provide over the wire advancement of the endocardial lead through the vasculature, the right atrium and the coronary sinus. Other techniques employ elongated pusher tools that have sufficient column strength applied against the lead body distal end and extending alongside the lead body and the over the guidewire. These techniques are relatively complex to execute. Moreover, the rotation of the active fixation helix at the lead distal end through rotation of the assembly can be problematic.

Further complications arise when a guide catheter is employed in the introduction procedure to facilitate advancement of such small diameter endocardial leads. When an over-the-wire technique is employed, the guidewire is first advanced through the skin incision, the vasculature, the right atrium, and into the coronary sinus. A guide catheter is introduced over the guidewire, and the lead is introduced over the guidewire and through the guide catheter lumen. When a stylet is employed, the guidewire is removed after the guide catheter is positioned, and the lead, stiffened by the stylet, is introduced through the guide catheter lumen. In either case, the distal electrode(s) is advanced out of the guide catheter distal lumen opening and advanced further into a vessel branching from the coronary sinus to an implantation site, and any distal fixation mechanism is affixed into the myocardium.

The subsequent removal of the stylet or guidewire and the guide catheter can impose forces on the lead body that detach the fixation mechanism and retract the electrode(s) from the desired implantation site. It is not possible to manually grip the proximal portion of the lead body extending out of the skin incision to hold it in place and counter these forces during withdrawal of the guide catheter and the stylet or guidewire as long as the lead body is within the guide catheter lumen. The guide catheter can be slowly retracted and slit or split along its length during the retraction to access the lead body, but detachment and electrode dislodgement can still occur.

It has been proposed in U.S. Pat. Nos. 6,356,791 and 6,671,560 to replace the guidewire or stylet with a specially shaped, removal wire that is longer than the guide catheter. The proximal connector assembly of the endocardial lead extends proximally from the guide catheter hub, and the lead removal wire distal end is inserted through the lead connector pin into the lead body lumen, whereby the removal wire distal end engages with the lead body lumen near the proximal connector pin. In a further approach embodied in the FINISHING WIRE® removal wire available from Guidant, Corp., Saint Paul, Minn., the removal wire is modified to have a tubular cap fixed in position proximal to the removal wire distal end that engages against the lead connector pin when the removal wire distal end is fully inserted into and engaged against the lead lumen. Force can be applied manually at the removal wire proximal end to hold the lead body proximal end stable as the guide catheter is retracted over the removal wire. The removal wire can be detached from the lead connector pin when the guide catheter is fully retracted onto the removal wire, revealing the lead connector pin. Thus, the removal wire must be somewhat longer than the guide catheter body and the length of the lead body lumen it is to be inserted into. Endocardial leads and guide catheters are marketed having a variety of lengths, resulting in the necessity of providing a removal wire tailored in length to the length of the lead body and guide catheter body. It is also necessary to fully seat the removal wire into the lead body lumen before the tubular cap engages the lead connector pin. It is desirable to maintain control of the connector pin even though the best position for the distal tip of the removal wire may not be at the distal tip of the lead. In certain cases, it may be desirable to only extend the removal wire part way through the lead body lumen resulting in an increased length of the removal wire extending proximally from the sleeve lumen. Such a length or removal wire can be unwieldy in the surgical field presenting difficulties in handling the lead, the removal wire, and the guide catheter during insertion of the removal wire into the lead body lumen and retraction of the guide catheter.

A further removal wire has been proposed in U.S. Pat. No. 6,625,496 that constitutes an extension sleeve that affixes to the outer surface lead connector pin. The extension sleeve has an outer diameter selected to fit within the guide catheter lumen and a lubricated outer surface, e.g., a hydrogel coating. In use, the guidewire or stylet employed to introduce the lead electrode(s) and fixation mechanism to the implantation site is removed, and the distal end of the extension sleeve is fitted to the lead connector pin. A long stylet or guidewire is extended through the axially aligned sleeve and lead body lumens so that it is seated or passes out of the distal lumen end opening and extends proximally of the extension sleeve apparently, to stabilize the lead body during removal of the guide catheter. The guide catheter is then retracted over the extension tube until the lead connector pin is exposed. Thus, the extension tube must be somewhat longer than the guide catheter body. In certain cases, it may be desirable to only extend the long stylet or guidewire part way through the lead body lumen resulting in an increased length of the stylet or guidewire extending proximally from the sleeve lumen. This length can also be unwieldy in the surgical field and present difficulties in handling the lead, the removal wire, and the guide catheter during insertion of the removal wire into the lead body lumen and retraction of the guide catheter.

Thus, a need remains for a system and method for introducing a small diameter cardiac lead lacking pushability and torqueability that enables advancement of the distal electrode through tortuous pathways into a wide variety of implantation sites in a heart chamber or in a coronary vessel of the left heart chambers and reliable fixation at the selected implantation site.

SUMMARY

The present invention satisfies this need in kit and method for implanting a cardiac lead of the types described above employing a lead stabilizer and extension wire that enables the withdrawal of a guide catheter over an electrical medical lead body without dislodging the distal electrode or a sensor from the implantation site and detaching any fixation mechanism. In use, the lead stabilizer and extension wire can be selectively adjusted in length, so that a distal segment of the lead stabilization and extension wire provides stabilization of the lead body while the guide catheter is retracted from the lead body and disposed over a proximal segment of the lead stabilization and extension wire.

Advantageously, the lead stabilizer and extension wire can be adjusted to any position within the lead body while providing positive engagement with the lead connector assembly to add the stiffness necessary to withdraw the guide catheter while preventing motion at the distal tip electrode(s) and fixation mechanism, if present, during withdrawal.

In a preferred embodiment, the lead stabilizer and retraction wire comprises an elongated wire sheath having a sheath lumen and a sheath outer diameter dimensioned to be received within the lead body lumen and an elongated core wire having a core wire body outer diameter sized to be received in the sheath lumen. The elongated core wire body is insertable into the sheath lumen to form the lead stabilization and extension wire having a desired extension wire length corresponding to the length of the wire sheath and the length of the core wire body extending outside the sheath lumen.

In a preferred embodiment, the core wire body and/or distal tip are preferably marked to indicate depth of insertion of the core wire body into the sheath lumen. Preferably, at least a distal surface area of the core wire body is marked to indicate depth of insertion of the core wire body into the sheath lumen.

In a preferred embodiment, the wire sheath has a lead clamp movable along the length of the wire sheath that can engage with the lead connector element and a sheath hub incorporating a friction element surrounding the sheath lumen, whereby the frictional engagement of the core wire with the friction element maintains the extension wire length.

The lead stabilizer and retraction wire is insertable through a proximal lumen opening into the lead body lumen enabling retraction of the guide catheter over the lead stabilization and extension wire while force is applied through the lead stabilization and extension wire to maintain the distal electrode at the implantation site.

In use, a distal wire segment of the lead stabilizer and extension wire is inserted into the lead body lumen to extend through a proximal portion of the lead body lumen and to dispose a proximal wire segment of the lead stabilizer and extension wire, substantially corresponding to the length of the guide catheter body, outside the lead body lumen. The lead clamp is affixed to the lead connector assembly to maintain the distal wire segment within the lead body lumen and the proximal wire segment outside the lead body lumen. A stabilization force is then applied to the lead stabilization and extension wire extending proximally from the guide catheter to stiffen and stabilize the lead body. The guide catheter is then retracted over the stabilized lead body to dispose the guide catheter body substantially over the proximal segment thereby exposing the lead connector assembly. The guide catheter can then be retracted off the proximal extension wire length, and the lead clamp can then be detached from the lead connector assembly. The lead clamp is released and the distal wire segment of the lead stabilization and extension wire is then retracted from the lead body lumen through the proximal lumen opening, while the lead connector assembly is held still, leaving the distal electrode at the implantation site and the lead connector assembly ready to be attached to an IMD or external medical device.

In a further aspect of the invention, a kit is provided that includes a guide tool adapted to be advanced through the proximal lumen opening into the lead body lumen during insertion and advancement of the pacing lead through the guide catheter lumen. The guide tool is manipulated to advance the distal electrode out of the guide catheter lumen and into contact with cardiac tissue to be stimulated, and is retracted and withdrawn from the lead body lumen and through the proximal lumen opening leaving the lead body extending through the guide catheter lumen. The guide tool may comprise one of a guidewire and a stiffening stylet of any of the known types.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be readily appreciated as the same becomes better understood by reference to the following detailed description when considered in connection with the accompanying drawings, in which like reference numerals designate like parts throughout the figures thereof and wherein:

FIG. 7 is a side view of a preferred embodiment of the elongated wire sheath of the lead stabilizer and retraction wire of the present invention;

FIG. 8 is a side cross-section view, taken along lines 8-8 of FIG. 7, of the wire sheath;

FIG. 10 is a partial perspective view of the pacing lead of FIGS. 2 and 3 fitted within the guide catheter lumen and the lead stabilization and extension wire extending through the lead body lumen and the guide catheter lumen as stabilization force is applied through the lead stabilization and extension wire and retraction force is applied to the guide catheter;

FIG. 11 is a side cross-section view, taken along lines 8-8 of FIG. 7, of the wire sheath having a modified lead clamp;

FIG. 12 is a partial side cross-section view of the modified lead clamp in relation to the proximal end of a modified lead connector pin advanced over the wire sheath; and FIG. 13 is a partial side cross-section view of the modified lead clamp screwed onto the proximal end of the modified lead connector pin advanced over the wire sheath.

Figure 1:
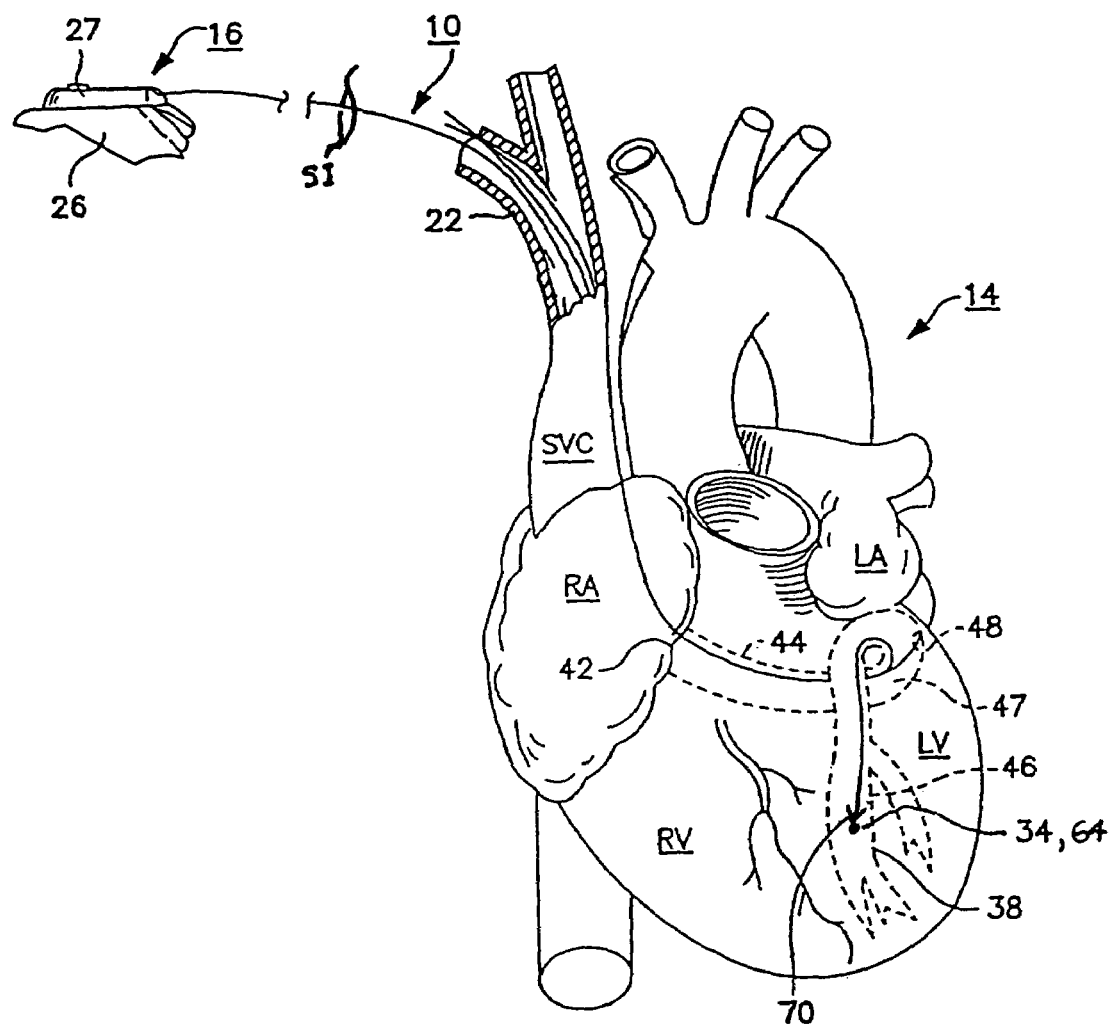
FIG. 1 is a schematic diagram of a heart from an anterior perspective illustrating the coronary venous system about an epicardial surface of the heart, including dashed lines depicting a portion of coronary venous system on an opposite, posterior epicardial surface of the heart.

The drawing figures are not necessarily to scale.

DETAILED DESCRIPTION

In the following detailed description, references are made to illustrative embodiments for carrying out the invention. It is understood that other embodiments may be utilized without departing from the scope of the invention. The invention and its preferred embodiments may be employed in implantation of unipolar, bipolar or multi-polar, endocardial, cardiac pacing or monitoring leads having one or more pace/sense electrode(s) or sense electrode(s), respectively, at or adjacent the distal lead end. Similarly, the invention and its preferred embodiments may be implemented in the implantation of cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a lead proximal end connector assembly. The proximal connector end assembly is adapted to be coupled to the connector assembly of an external medical device, including an external pacemaker or monitor, or an implantable medical device, including an IPG for pacing, cardioversion/defibrillation or both or an implantable monitor. Therefore, it will be understood that the devices and methods for introduction of a cardiac lead of the present invention can be employed to introduce permanently implantable and temporary cardiac leads of any of these types.

The lead stabilization and retraction wire and methods of the present invention are particularly useful in introducing such small diameter cardiac leads that have a stylet or guidewire lumen and are so flexible and possess such low column strength, pushability and torqueability that the lead distal end cannot be advanced transvenously and positioned at the desired implantation site without use of a guide catheter.

In FIG. 1, heart 14 includes the upper heart chambers, the right atrium (RA) and left atrium (LA), and the lower heart chambers, the right ventricle (RV), and the left ventricle (LV). The CS is also depicted schematically in FIG. 1 extending from the opening 42 in the RA and extending laterally around the atria as the cardiac vein 44 and into the anterior interventricular vein 46 descending inferiorly along the LV. FIG. 1 also schematically depicts of a cardiac lead 10 introduced into implantation sites of the coronary vessels branching from the coronary sinus (CS). The cardiac lead 10 is introduced to the implantation sites in the cardiac blood vessels or chambers of the heart 14 through a tortuous pathway from a skin incision SI and venotomy made through the vasculature or venous system, e.g., the right or left cephalic vein, other subclavian branches or the external or internal jugular vein, in a manner well known in the art. For simplicity of illustration, a unipolar right heart cardiac lead 10 is shown in FIG. 1 extending through the skin incision SI, the vasculature leading to the superior vena cava (SVC) 22 then inferiorly through the RA and CS and into the CS or a vessel branching therefrom.

The proximal lead connector elements of cardiac lead 10 are schematically illustrated coupled in each instance to an implantable medical device (IMD) 16 of any of the above noted types. The IMD 16 (depicted partially) is implanted subcutaneously, i.e., below the skin, after it is connected to the lead connector element(s) and includes electronic components and a power supply enclosed with a housing 26 and a connector block 27. Connector block 27 has one or more bore for receiving the proximal lead connector element(s) of the cardiac lead 10.

In FIG. 1, the schematically illustrated cardiac lead 10 can have a unipolar, bipolar or multi-polar configuration and can be fabricated with pace/sense and/or cardioversion/defibrillation electrodes. Alternatively or additionally, the cardiac lead 10 can simply bear EGM sensing electrodes and/or physiologic sensors. The cardiac lead 10 is formed having an elongated lead body extending between a connector element at a lead body proximal end (depicted inserted within a bore of the IMD connector block 27) and a lead body distal end. An electrode 34 is also supported at or adjacent to the lead body distal end, and a lead conductor extends within the lead body between the connector element and the electrode 34. It will be understood that the kit and methods of the present invention for introduction of the cardiac lead 10 to an implantation site in a coronary vessel of the heart 14 can be employed with any form of cardiac lead 10 that may or may not be formed having an active fixation mechanism or a passive fixation mechanism.

Figure 2:
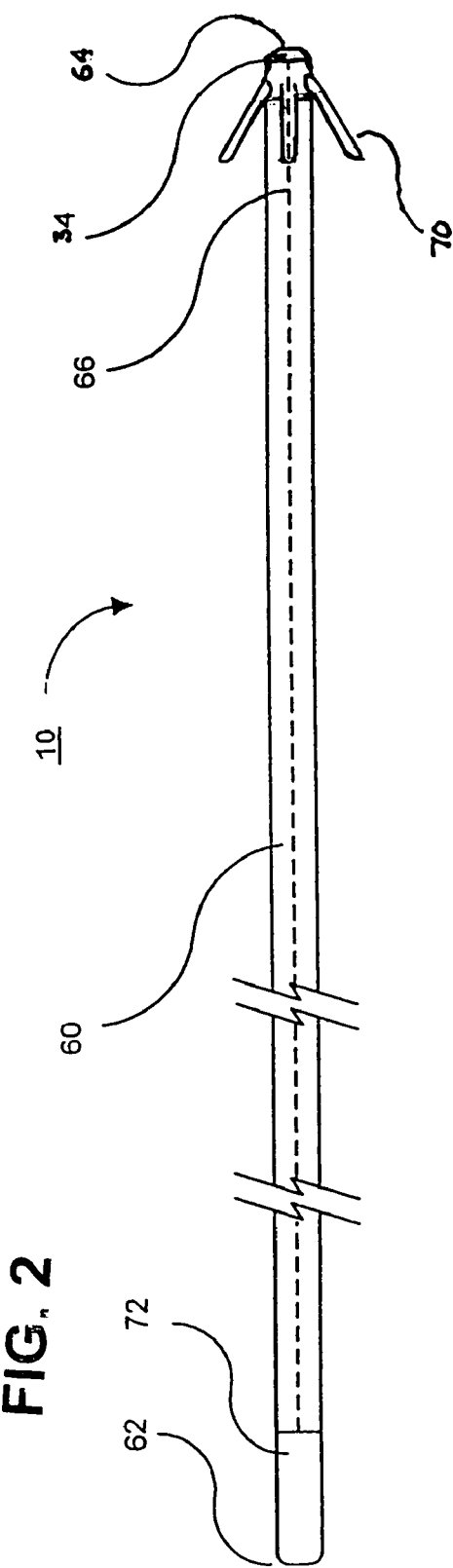
FIG. 2 is a plan view, in partial exposed section, of an exemplary pacing lead that can be introduced and affixed in the coronary venous system employing the devices and methods of the present invention.

By way of example, and without limitation, cardiac lead 10 is depicted in FIGS. 1 and 2 having a pace/sense electrode 34 at the lead body distal end 64 that is maintained at the implantation site by soft, pliant, passive fixation tines 70 extending outward of the lead body just proximal to the lead body distal end 64. An additional pace/sense electrode or cardioversion/defibrillation electrode may be located along the lead body proximal to the distal pace/sense electrode 34. Thus, the distal cardiac electrode 34 is at or adjacent to (i.e., contiguous to) the lead body distal end 64.

In FIG. 1, the lead body distal end 64 and pace/sense electrode 34 of cardiac lead 10 are introduced through the SVC and RA chamber and the ostium of the CS to extend alongside the LA chamber and the LV. The distal electrode (s) 34 can be located as depicted deep within the anterior interventricular vein 46 at LV implantation site 38 adjacent to the LV for LV stimulation and/or sensing applications. The distal electrode(s) can be located in the cardiac vein 47 at an implantation site 48 adjacent to the LA to provide LA stimulation and/or sensing applications. The soft, pliant, passive fixation tines 70 are adapted to bear against the coronary vessel wall at the implantation site 38, 48 or other site within the coronary vessels and provide passive fixation therewith.

Figure 3:
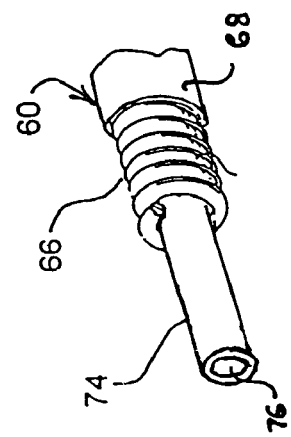
FIG. 3 is a cutaway view of the interior of the lead body of the exemplary pacing lead of FIG. 2.

An exemplary unipolar cardiac lead 10 that can be implanted in the sites depicted in FIG. 1 is depicted in greater detail in FIGS. 2 and 3. The cardiac lead 10 includes an elongated lead body 60 extending between a connector element 72 of a connector assembly at a lead body proximal end 62 and the distal pace/sense electrode 34 at the lead body distal end 64. The passive fixation tines 70 extend obliquely and proximally from the lead body distal end 64. A lead conductor 66 extends within the lead body 60 between the connector element 72 and the distal pace/sense electrode 34.

It will be understood that active fixation elements, e.g., prongs or hooks or a distally extending fixation helix, or a passive fixation mechanism, e.g., a particularly shaped distal segment of the lead body like that disclosed in commonly assigned U.S. Pat. No. 5,999,858, may be substituted for the soft, pliant, passive fixation tines 70, and such a cardiac lead can advantageously be implanted employing the lead stabilization and extension wire, kit, and methods of the present invention described further below. For example, the cardiac lead 10 depicted in FIG. 2 can be the. MEDTRONIC® Attain™ OTW Model 4193 left heart pacing lead, which can be advantageously implanted in a selected implantation site depicted in FIG. 1 employing the lead stabilization and extension wire and kit and method of the present invention. The lead body lumen of the Model 4193 left heart pacing lead accepts a stiffening stylet or a guidewire, and the lead body is angled in distal segments to provide enhanced steerability and stable fixation in a range of coronary vessels, without the need for tines or an active fixation mechanism. In addition, the lead stabilization and extension wire and kit and method of the present invention present may be advantageously employed in the implantation of a cardiac lead that does not possess any form of active or passive fixation.

The lead body 60 can be formed in a variety of ways, and one example is depicted in FIG. 3. The illustrated exemplary lead body 60 comprises a single-filar or multi-filar helical conductor 66 that is wound into a coil about a flexible non-conductive inner tube 74 within the lumen of a flexible, electrically insulating outer sheath 68 formed of silicone rubber or polyurethane. The inner tube 74 can be eliminated, but in either case, a lead body lumen 76 is provided that extends from a proximal lumen end opening at lead body proximal end 62 to the lead body distal end 64. The connector element 72 is a hollow connector pin having a pin lumen axially aligned with the lead body lumen 76 providing the proximal lumen end opening. The distal end of the lead body lumen 76 is blocked at lead body distal end 64 if the lead 10 is intended to be implanted employing a stiffening stylet. A distal end opening of the lumen 76 is formed in the lead body distal end 64 if the lead body 60 is intended to be advanced over a guidewire inserted through lead body lumen 76 or using a stiffening stylet. In certain designs, the conductor 66 may take the form of a stranded wire that is not coiled, and a separate lead body lumen is formed extending side-by-side with the lead conductor and aligned with the pin lumen.

Figure 4:
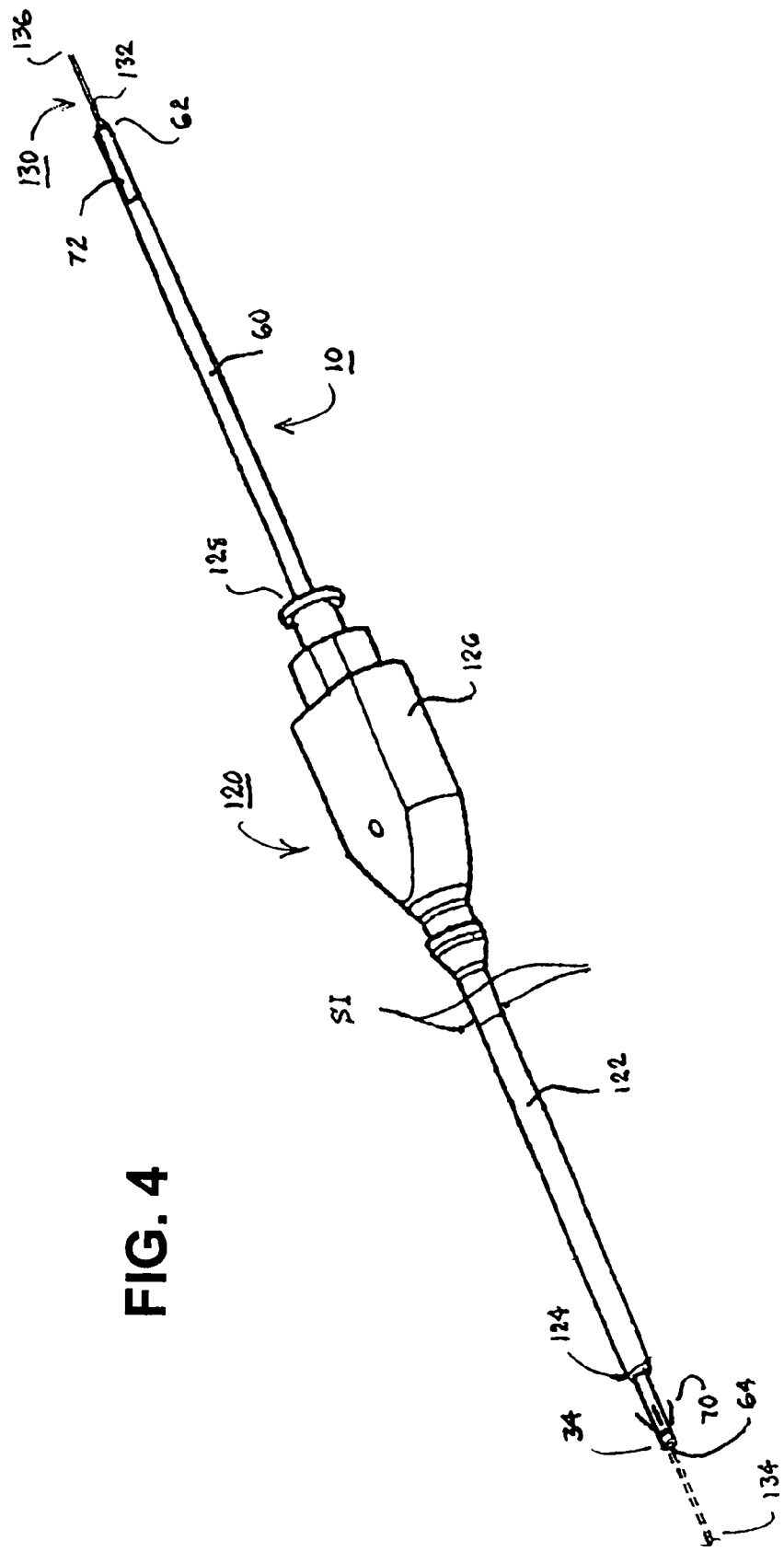
FIG. 4 is a perspective view of the pacing lead of FIGS. 2 and 3 fitted within a guide catheter lumen and with a guide tool comprising a guidewire or stylet extending through or into the lead body lumen.

Turning to FIG. 4, the devices and methods of the present invention enables the implantation of a small diameter lead body 60 in the range of 1 French (0.33 mm) to 3 French (1.00 mm) employing a guide catheter 120 and a guide tool 130. It will be understood that the over-the-wire guide catheter 120 can be sized to facilitate implantation of larger diameter lead bodies exceeding 3 French in diameter.

The guide catheter 120 shown in FIG. 4 can be of any standard or non-standard form having at least an elongated, typically tubular, guide catheter body 122 extending between a guide catheter distal end 124 and a proximal guide catheter hub 126. The length of the guide catheter body 122 is selected to extend from the skin incision SI through an incision into a selected vein, the selected route through the vasculature, the SVC, the RA and into at least a portion of the CS. Suitable guide catheter body lengths may be in the range of 40 cm to 60 cm. At least one guide catheter lumen 128 extends between a proximal catheter lumen end opening in the guide catheter hub 126 and a distal catheter lumen end opening at the catheter distal end 124. The guide catheter lumen 128 has a catheter lumen diameter that is large enough to receive the lead body 60 and the lead stabilizer and extension wire of the present invention. The guide catheter lumen diameter may be in the range of 4.0 French (1.3 mm) to 7.5 French (2.5 mm).

The guide tool 130 shown in FIG. 4 inserted into the lead body lumen 76 may comprise one of a guidewire and a stiffening stylet of any of the known types that typically comprises a guidewire body 132 that extends between a distal guidewire body end 134 and a proximal guidewire body end 136. The guide tool 130 is adapted to be advanced through the proximal lumen end opening into the lead body lumen 76 during insertion and advancement of the pacing lead 10 through the guide catheter lumen 128. The guide tool 130 is manipulated to advance the distal pace/sense electrode 34 and passive fixation tines 70 out of the guide catheter lumen 128 to dispose the distal pace/sense electrode 34 in contact with the vessel wall adjacent the cardiac tissue to be sensed and/or stimulated. The guide tool 130 is then retracted and withdrawn from the lead body lumen 76 and through the proximal lumen opening leaving the lead body 60 extending through the guide catheter lumen 128. For convenience of illustration, the guide tool 130 is depicted in FIG. 4 in broken lines as a guidewire extending distally from a distal lumen end opening of lead body lumen 76, although the guide tool 130 may be a stiffening stylet disposed within the lead body lumen 76.

The guide tool 130 is intended to be retracted and withdrawn from the lead body lumen 76 out through the proximal lumen opening leaving the lead body 60 extending through the guide catheter lumen 128 after the distal pace/sense electrode 34 is located at the desired implantation site. The guide catheter 120 remains in place with the guide catheter hub 126 and the proximal lead connector pin 72 located outside the skin incision.

Figure 5:
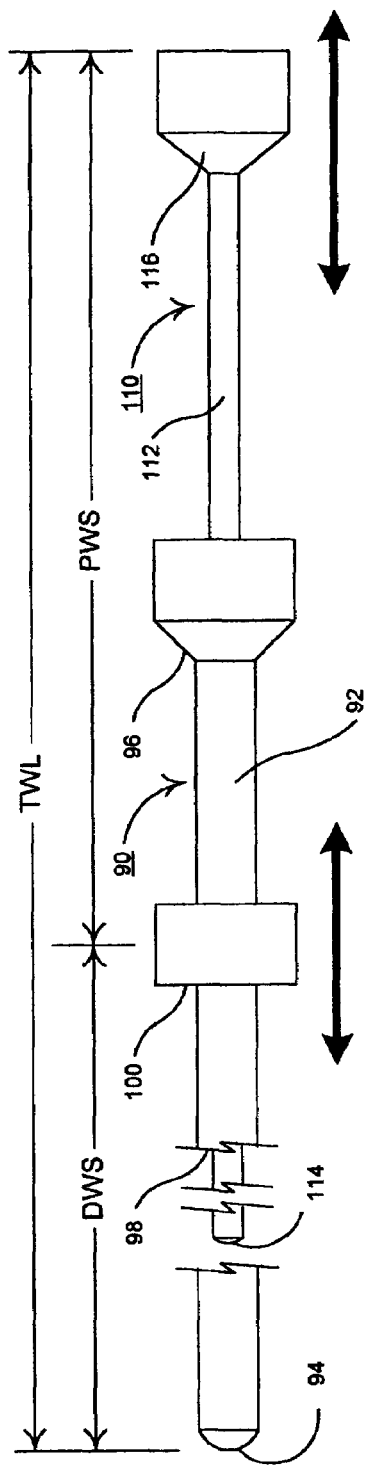
FIG. 5 is a side view of a preferred embodiment of a lead stabilization and extension wire comprising an elongated core wire fitted into the sheath lumen of the elongated wire sheath in a telescoping fashion enabling selecting a proximal wire segment insertable into the lead body lumen for stabilization and selecting a distal wire segment extending from the lead connector ring that the guide catheter of FIG. 4 is retracted over.

Turning to FIG. 5, a lead stabilizer and extension wire 140 that enables the withdrawal of guide catheter 120 over the electrical medical lead body 60 without retracting the distal electrode (or a sensor) from the implantation site and detaching any fixation mechanism, e.g., passive fixation tines 70, is depicted. The lead stabilizer and retraction wire 140 comprises an elongated wire sheath 90 and an elongated core wire 110 arranged in a telescopic manner providing a selected total wire length TWL. In use, the lead stabilizer and extension wire 140 can be selectively adjusted in total wire length TWL, so that a distal wire segment DWS of the lead stabilization and extension wire 140 fits into the lead body lumen 76 to provide stabilization of the lead body 60 while the guide catheter 120 is retracted from the lead body 60 and disposed over a proximal wire segment PWS of the lead stabilization and extension wire 140.

Figure 6:
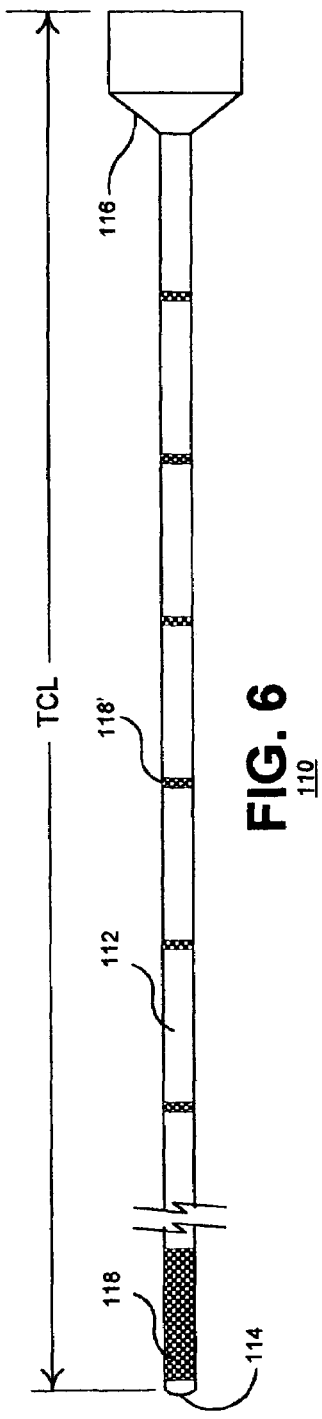
FIG. 6 is a side view of a preferred embodiment of the elongated core wire insertable into the sheath lumen of the wire sheath to form the lead stabilization and extension wire.

The elongated core wire 110, also shown in FIG. 6, comprises a length of metal or plastic core wire body 112 extending between a core wire distal end 114 and a proximal core wire hub 116 and has total core wire length TCL. The core wire body 112 may be uniform in diameter or may vary in diameter along its length to vary its stiffness and terminate in a ball tip. The maximum core wire body diameter is selected to fit within the sheath lumen 98 of the wire sheath 90 as shown in FIG. 5. The maximum core wire body diameter may be in the range of 0.45 mm to 0.53 mm, for example. The core wire hub diameter is preferably smaller than the diameter of the guide catheter lumen 128, to enable retraction of the guide catheter 120 over the core wire hub 116.

In a further preferred embodiment, the core wire body 112 may have a distinctly colored distal segment 118 that alerts the user, as the core wire body 112 is retracted proximally, to halt retraction to maintain at least the distal segment 118 of the core wire body 112 within the sheath lumen 98.

Preferably, the core wire body 112 is instead or also marked with periodic marks 118' to indicate depth of insertion of the core wire body 112 into the sheath lumen 98.

The wire sheath 90, also shown in FIGS. 7 and 8, comprises an elongated sheath body 92 extending between a sheath distal end 94 and a proximal sheath hub 96 and has total sheath length TSL. The outer diameter of sheath body 92 is dimensioned to be received within the lead body lumen 76. A sheath lumen is defined sheath body lumen 98 and a sheath hub lumen 104 of sheath hub 96 that is axially aligned with sheath body lumen 98. The sheath body lumen 98 extends distally from sheath hub 96 to a plug 94 forming the sheath body distal end. The sheath lumen 98 has a sheath lumen diameter that is large enough to receive the core wire body 112.

A friction ring 106 is preferably fitted into the sheath hub lumen 104 having an inner diameter that is dimensioned to provide an interference fit against the core wire body 112. The friction ring 106 may comprise a soft rubber grommet cemented to the inner surface of the hub lumen 104 or a surface treatment of the hub lumen 104. The friction ring surface frictionally engages the core wire body 112 to hold it in position in the sheath lumen 98 with a force that can be overcome to manually reposition the core wire body 112 within the sheath lumen 98.

The wire sheath 90 further comprises a lead clamp 100 that is movable along the length of the wire sheath body 98 between the sheath body distal end 94 and the sheath hub 96 (or a more limited range along sheath body 98). The lead clamp 100 may comprise a tube or ring of resilient material having a ring lumen that is dimensioned to interference fit against the circumference of the sheath body 92. The ring lumen surface of the lead clamp 100 may comprise a relatively soft polymer that frictionally engages the surface of the sheath body 98 to hold the lead clamp in a selected position. The engagement force can be manually overcome to move the lead clamp along the surface of the sheath body 98. An annular receptacle or gap 102 is also formed around the ring lumen on the distal side of the lead clamp 100 that is dimensioned to receive and fit over the outer surface of the lead connector element 72 as shown in FIGS. 9 and 10 and described further below.

The lead clamp 100 can be formed of a single piece of silicone rubber or soft durometer polyurethane that has a lumen diameter sized to interference fit against the sheath body 92 and a gap lumen diameter of gap 102 sized to interference fit against and engage the connector pin 72 of cardiac lead 10 to provide positive retention and engagement. It will be understood that the connector pin outer surface may be modified to have a surface roughness to enhance frictional engagement with the surface of annular gap 102.

In use, the core wire body 112 is inserted into the sheath lumen 98 to form the lead stabilization and extension wire 140 shown in FIG. 5 having a desired total wire length TWL corresponding to the total sheath length TSL of the wire sheath and the length of the core wire 110 extending outside the sheath lumen 98. Thus, the total wire length may vary between about the total sheath length TSL and the sum of the total sheath length TSL and the total core wire length TCL. The relative positions of the lead clamp 100 along the sheath body 92 and the exposed length of the core wire body 112 dictate the lengths of the distal wire segment DWS and the proximal wire segment PWS and the total wire length TWL shown in FIG. 5. The frictional engagement of the lead clamp 100 against the sheath body 98 and the friction ring 106 against the core wire body 112 maintains the selected segment lengths.

Figure 9:
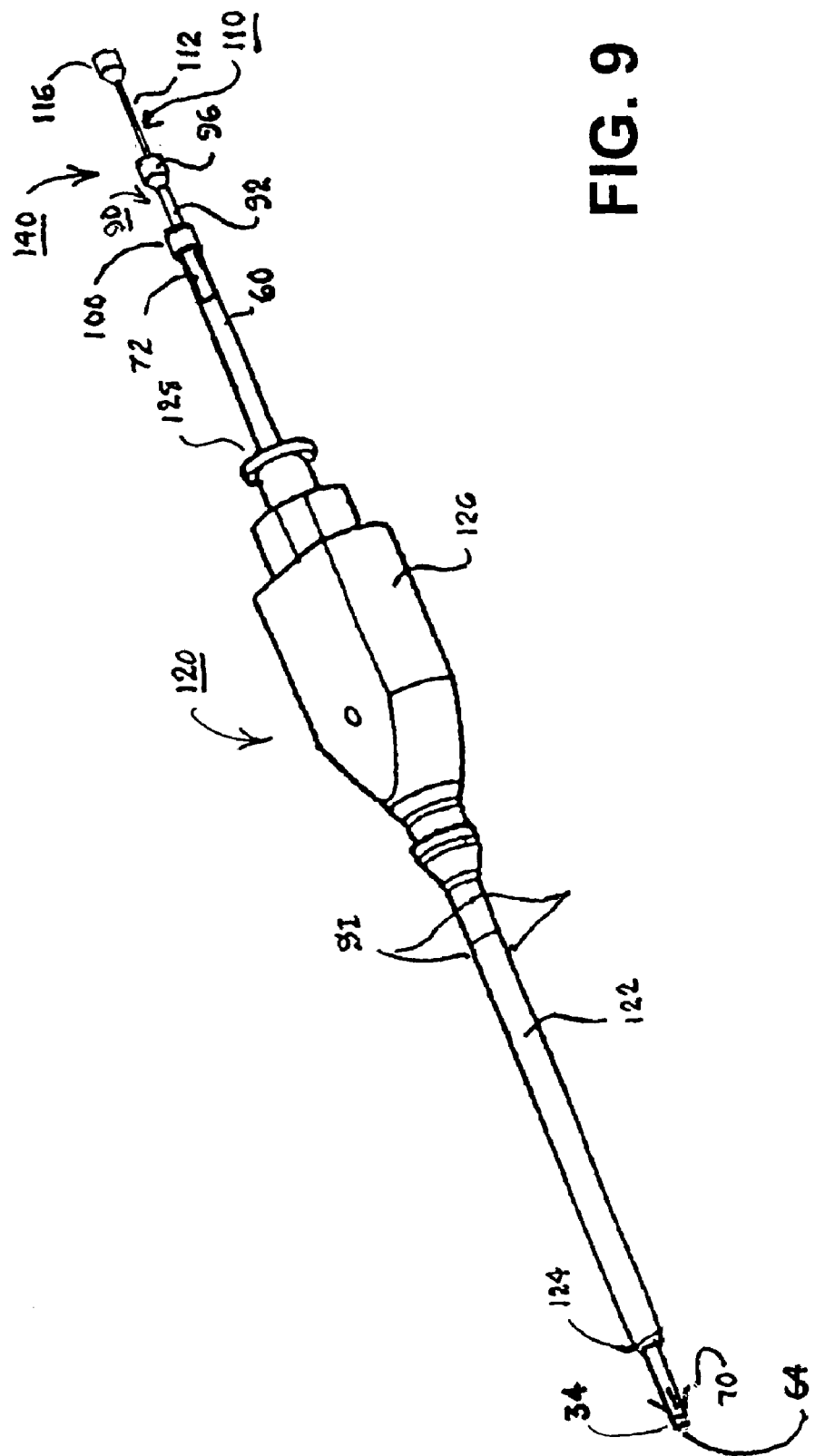
FIG. 9 is a perspective view of the pacing lead of FIGS. 2 and 3 fitted within the guide catheter lumen and the distal wire segment inserted into the lead body lumen for stabilization and the proximal wire segment extending from the lead connector ring.

Turning to FIG. 9, the lead stabilizer and retraction wire 140 is inserted into the lead body lumen 76 to enable retraction of the guide catheter 120 over the lead body 60 and onto a proximal wire segment PWS of the stabilization and extension wire 140. A distal wire segment DWS of the lead stabilizer and extension wire 140 is inserted into the lead body lumen 76 to extend through a proximal portion of the lead body lumen 76 selected by the physician. The proximal wire segment PWS of the stabilizer and extension wire 140 extends proximally from the lead proximal end 62 outside the skin incision SI. The annular slot 102 of the lead clamp 100 is fitted over the proximal end of the lead connector pin 72 and frictionally engages it.

The length of the proximal wire segment PWS may initially be set to exceed the length of the guide catheter 120, or the PWS length may be periodically adjusted by selective retraction of either or both of the lead clamp 100 and the core wire hub 116. Further adjustment of the lead clamp 100 is not possible after the guide catheter 120 is retracted proximally over the lead clamp 100 and the lead connector pin 78. Then, the PWS length can only be adjusted by retracting the core wire body 92 proximally from the sheath lumen 98 while manually holding the sheath hub 96 steady. Further proximal retraction of the core wire body 92 from the sheath lumen 98 is not possible once the guide catheter 120 is retracted proximally over the sheath hub 96. So, it is preferable to select the PWS length to accommodate the length of the guide catheter 120 before moving the guide catheter 120 proximally over the lead stabilizer and extension wire 140.

As shown in FIG. 10, the guide catheter 120 is carefully retracted over the lead body 60 through application of a retraction force HF to the guide catheter hub 126 while a stabilization force SF is applied to the lead stabilization and extension wire 140 extending proximally from the guide catheter lumen 128 to hold it still. The stabilization force SF applied to the lead stabilization and extension wire 140 extending proximally from the guide catheter lumen 128 simply needs to be great enough to maintain the length of the distal wire segment DWS in order to stabilize the lead body 60 as the guide catheter 120 is retractod. The retraction disposes the guide catheter body 122 substantially over the proximal wire segment PWS thereby exposing the lead clamp 100 and the lead connector assembly including connector ring 72 distal to the guide catheter body distal end 124. During such retraction, the lead clamp 100 affixed to the lead connector ring 72 maintains the distal wire segment DWS within the lead body lumen 76 and the proximal wire segment PWS outside the lead body lumen 76.

The guide catheter 120 is thereby retracted off the lead body 60, and the lead clamp 100 can then be detached from the lead connector pin 72. The distal wire segment DWS of the lead stabilization and extension wire 140 is then retracted from the lead body lumen 76 through the proximal lumen end opening, while the lead connector assembly is held still. The distal pace/sense electrode 34 and passive fixation tines 70 remain at the implantation site, and the lead connector assembly is ready to be attached to an IMD or external medical device, e.g., the IMD 16 of FIG. 1.

It will also be understood that the lead clamp 100 may take other forms, e.g., a collet mechanism adapted to be rotated or adjusted manually to tighten against or release the connector pin 72 of cardiac lead 10 to provide positive retention and engagement. Or, the lead connector pin exterior surface or pin lumen interior surface may be modified to have mating elements, e.g., splines or screw threads, that mate with corresponding mating elements, e.g., splines or screw threads, formed within gap 102 or on a distal portion of the lead clamp 100. In this case, a more rigid metal or plastic insert would be fitted into the gap 102 to make positive retention and engagement over at least a portion of the connector pin or a more distal portion of the connector assembly or into the pin lumen.

An exemplary modified lead clamp 200 adapted to be employed with a modified lead connector pin 272 of lead 210 is depicted in FIGS. 11-13. The modified lead connector pin 272 is formed with male spiral pin threads 224 over its outer surface that mate with female spiral lead clamp threads 204 formed within annular gap 202. As shown in FIG. 12, the sheath body 92 is advanced into the connector pin lumen and lead body lumen 276 to locate a selected distal wire segment DWS therein. In the step illustrated in FIG. 9 as described above, the connector pin 272 is grasped in FIG. 12, and the lead clamp 200 is moved over the sheath body 92 against the lead proximal end 262. In FIG. 13, the lead clamp 200 is also grasped and rotated to screw the female spiral lead clamp threads 204 onto the male spiral pin threads 224. Thus, a positive retention and engagement of the lead connector pin 272 is accomplished during the steps of removing the guide catheter 120 as described above with respect to FIGS. 9 and 10. The lead clamp 200 is also grasped and rotated in the opposite direction to unscrew the female spiral lead clamp threads 204 from the male spiral pin threads 224 prior to application of the stabilization force SF and the retraction force RF in FIG. 10 as described above. It will be understood that the depicted screw threads could be located within the pin lumen to mate with screw threads on a distal portion lead clamp 200 sized to fit within the pin lumen.

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiments without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

What is claimed is:

1. A lead stabilization and extension wire to be employed to facilitate retraction of a guide catheter over an implanted cardiac lead of a type comprising a lead body enclosing a lead body lumen and extending from a proximal connector assembly having a lead connector element to a distal electrode and adapted to be disposed at an implantation site within a patient's heart, and wherein the implanted cardiac lead has been placed by introduction through a lumen of a guide catheter passed through a skin incision of a patient providing access to the patient's vasculature, the lead stabilization and extension wire being adapted to be inserted into a proximal lumen opening of the lead body lumen to stabilize the lead body and distal electrode position during retraction of the guide catheter over the lead body, comprising:

a wire sheath having a sheath outer diameter dimensioned to be received within the lead body lumen and a sheath lumen within a sheath body extending between sheath body proximal and distal ends;

a lead clamp coupled to the wire sheath for engaging the implanted cardiac lead; and an elongated core wire having a core wire body extending between proximal and distal core wire body ends and a core wire body outer diameter sized to be received in the sheath lumen, wherein the elongated core wire upon insertion into the sheath lumen engages the wire sheath and provides stabilization of the implanted cardiac lead through a stabilization force applied at the core wire body proximal end.

2. The lead stabilization and extension wire of claim 1, wherein the stabilization force applied at the core wire body proximal end is transferred through the a lead clamp to the implanted cardiac lead to maintain the distal electrode at the implantation site while the guide catheter is retracted over the lead body.

3. The lead stabilization and extension wire of claim 2, wherein the lead clamp movable along the length of the wire sheath that can positively engage with and retain the lead connector element to stabilize a distal sheath segment disposed within the lead body lumen.

4. The lead stabilization and extension wire of claim 3, wherein the wire sheath further comprises a sheath hub incorporating a friction element surrounding the sheath lumen and providing frictional engagement with the core wire body to maintain a distal segment of the core wire body within the sheath lumen and a proximal segment of the core wire body outside the sheath lumen, whereby proximal wire segment length is maintained.

5. The lead stabilization and extension wire of claim 2, wherein the wire sheath further comprises a sheath hub incorporating a friction element surrounding the sheath lumen providing frictional engagement with the core wire body to maintain a proximal segment of the core wire body outside the sheath lumen.

6. The lead stabilization and extension wire of claim 1, wherein the lead clamp movable along the length of the wire sheath that can positively engage with and retain the lead connector element to stabilize a distal sheath segment disposed within the lead body lumen and maintain the distal wire segment length.

7. The lead stabilization and extension wire of claim 6, wherein the wire sheath further comprises a sheath hub incorporating a friction element surrounding the sheath lumen providing frictional engagement with the core wire body to maintain a distal segment of the core wire body within the sheath lumen and a proximal segment of the core wire body outside the sheath lumen, whereby the friction element maintain the proximal wire segment length.

8. The lead stabilization and extension wire of claim 6, wherein the lead clamp and the lead connector element have mating elements that engage one another to positively engage with and retain the lead connector element to stabilize a distal sheath segment disposed within the lead body lumen and maintain the distal wire segment length.

9. The lead stabilization and extension wire of claim 1, wherein the wire sheath further comprises a sheath hub incorporating a friction element surrounding the sheath lumen providing frictional engagement with the core wire body to maintain a proximal segment of the core wire body outside the sheath lumen.

10. The lead stabilization and extension wire of claim 1, wherein the core wire body is marked to indicate depth of insertion of the core wire body into the sheath lumen.

11. A kit for implanting a cardiac lead of the type comprising an elongated lead body enclosing a lead body lumen, the lead body extending from a proximal connector assembly to a distal electrode, through a skin incision of a patient accessing the vasculature to dispose the distal electrode at an implantation site within a coronary vessel of the heart of the patient the kit comprising:
　a guide catheter extending between a guide catheter proximal end and a guide catheter distal end adapted to be advanced through the incision and the vasculature until a distal end of the guide catheter is located in the coronary vessel and the proximal end of the guide catheter is outside the skin incision, the guide catheter having a guide catheter outer diameter sized to be advanced through the vasculature and at least a portion of the coronary vessel and a guide catheter lumen sized to receive the cardiac lead;
　a guide tool adapted to be advanced through the proximal lumen opening into the lead body lumen during insertion and advancement of the cardiac lead through the guide catheter lumen, manipulated to advance the distal electrode out of the guide catheter lumen and into contact with cardiac tissue to be stimulated, and retracted and withdrawn from the lead body lumen and through the proximal lumen opening leaving the lead body extending through the guide catheter lumen; and
　a lead stabilization and extension wire having a distal wire segment adapted to be inserted through the proximal lumen opening into the lead body lumen after withdrawal of the guide tool to facilitate retraction of the guide catheter over the lead body further comprising;
　a wire sheath having a sheath outer diameter dimensioned to be received within the lead body lumen and a sheath lumen within a sheath body extending between sheath body proximal and distal ends; and
　　an elongated core wire having a core wire body extending between proximal and distal core wire body ends and a core wire body outer diameter sized to be received in the sheath lumen,
　　wherein the elongated core wire is insertable into the sheath lumen to selectively adjust the length of the lead stabilization and extension wire between the core wire body proximal end and the sheath body distal end,
　　wherein the wire sheath further comprises a lead clamp movable along the length of the wire sheath that can positively engage with and retain the lead connector element to stabilize a distal sheath segment disposed within the lead body lumen and maintain the distal wire segment length.

12. The kit of claim 11, wherein the distal wire segment of the lead stabilization and extension wire provides stabilization of the lead body through stabilization force applied at the core wire body proximal end through the lead stabilization and extension wire to maintain the distal electrode at the implantation site while the guide catheter is retracted from the lead body and disposed over a proximal wire segment of the lead stabilization and extension wire.

13. The kit of claim 12, wherein the wire sheath further comprises a lead clamp movable along the length of the wire sheath that can positively engage with and retain the lead connector element to stabilize a distal sheath segment disposed within the lead body lumen and maintain the distal wire segment length.

14. The kit of claim 13, wherein the wire sheath further comprises a sheath hub incorporating a faction element surrounding the sheath lumen providing frictional engagement with the core wire body to maintain a distal segment of the core wire body within the sheath lumen and a proximal segment of the core wire body outside the sheath lumen, whereby the friction element maintain the proximal wire segment length.

15. The kit of claim 12, wherein the wire sheath further comprises a sheath hub incorporating a friction element surrounding the sheath lumen providing frictional engagement with the core wire body to maintain a proximal segment of the core wire body outside the sheath lumen.

16. The kit of claim 11, wherein the lead clamp and the lead connector element have mating elements that engage one another to positively engage with and retain the lead connector element to stabilize a distal sheath segment disposed within the lead body lumen and maintain the distal wire segment length.

17. The kit of claim 11, wherein the wire sheath further comprises a sheath hub incorporating a friction element surrounding the sheath lumen providing frictional engagement with the core wire body to maintain a distal segment of the core wire body within the sheath lumen and a proximal segment of the core wire body outside the sheath lumen, whereby the friction element maintain the proximal wire segment length.

18. The kit of claim 11, wherein the core wire body is marked to indicate depth of insertion of the core wire body into the sheath lumen.

19. The kit of claim 11, wherein the wire sheath further comprises a sheath hub incorporating a friction element surrounding the sheath lumen providing frictional engagement with the core wire body to maintain a proximal segment of the core wire body outside the sheath lumen.

20. A method for installing an intravenous cardiac lead having a lead body lumen within a patient, comprising:
　advancing a guide catheter having a guide catheter lumen through a skin incision and the vasculature until a distal end of the guide catheter is located in a coronary vessel of the heart;
　advancing the cardiac lead through the guide catheter lumen to position a distal end of the cardiac lead at an implantation site, wherein at least a portion of the cardiac lead is maintained within the guide catheter lumen;
　providing a lead stabilization and extension wire comprising a wire sheath having a sheath outer diameter dimensioned to be received within the lead body lumen and a sheath lumen within a sheath body extending between sheath body proximal and distal ends and an elongated core wire having a core wire body extending between proximal and distal core wire body ends and a core wire body outer diameter sized to be received in the sheath lumen,
　moving the elongated core wire with respect to the sheath lumen to selectively adjust the length of the lead stabilization and extension wire between the core wire body proximal end and the sheath body distal end,
　inserting a distal wire segment of the lead stabilization and extension wire into the cardiac lead lumen to stabilize the cardiac lead;

retracting the guide catheter from the cardiac lead lumen and onto a proximal wire segment of the lead stabilization and extension wire;

retracting the distal wire segment of the lead stabilization and extension wire from the lead lumen;

applying a stabilization force to the lead stabilization and extension wire to maintain the distal end of the cardiac lead at the implantation site while retracting the guide catheter from the cardiac lead and over the proximal wire segment of the lead stabilization and extension wire; and wherein the wire sheath further comprises a lead clamp along the length of the wire sheath that can positively engage with and retain the cardiac lead and further comprising moving the lead clamp along the length of the wire sheath into engagement with the cardiac lead to establish and maintain a distal wire segment length while retracting the guide catheter from the cardiac lead and over the proximal wire segment of the lead stabilization and extension wire.

21. The method of claim 20, wherein the wire sheath further comprises a sheath hub incorporating a friction element surrounding the sheath lumen providing frictional engagement with the core wire body to maintain a distal segment of the core wire within the sheath lumen and a proximal segment of the core wire outside the sheath lumen, whereby the friction element maintain the proximal wire segment length.

22. The method of claim 20, wherein the wire sheath further comprises a sheath hub incorporating a friction element surrounding the sheath lumen providing frictional engagement with the core wire body to maintain a proximal segment of the core wire outside the sheath lumen.

23. The method of claim 20, wherein the cardiac lead has a lead connector element at a proximal end and wherein the lead clamp and the lead connector element have mating elements that engage one another to positively engage with and retain the lead connector element to stabilize the cardiac lead and further comprising rotating the lead clamp with respect to the lead connector element to engage or disengage the mating elements.

24. The method of claim 20, wherein the step of advancing the cardiac lead further comprises:

advancing a stiffening stylet into the lead lumen;

inserting and advancing the cardiac lead and stylet through the guide catheter lumen to advance the distal end out of the guide catheter lumen and adjacent tissue to be stimulated; and retracting the stylet from the lead lumen.

25. The method of claim 20, further comprising:

advancing a guidewire through the incision and the vasculature until a distal end of the guidewire is located in the coronary vessel and the proximal end of the guidewire is outside the skin incision, and wherein:

the step of advancing the guide catheter comprises advancing the guide catheter over the guidewire; and the step of advancing the cardiac lead comprises:

inserting the proximal end of the guidewire through a distal lumen end opening the lead lumen;

advancing the lead distally over the guidewire and through the guide catheter lumen to position the distal end of the cardiac lead at an implantation site; and retracting the guidewire from the lead lumen.

26. A method of implanting a cardiac lead of the type comprising an elongated lead body extending from a proximal connector assembly to a distal electrode enclosing a lead conductor and a lead body lumen having a proximal lumen opening through a skin incision of a patient accessing the vasculature to dispose the distal electrode at an implantation site within a coronary vessel of the heart of the patient, the method comprising:

advancing a guide catheter through the incision and the vasculature until a distal end of the guide catheter is located in the coronary vessel and the proximal end of the guide catheter is outside the skin incision, the guide catheter having a guide catheter outer diameter sized to be advanced through the vasculature and at least a portion of a coronary vessel and a guide catheter lumen sized to receive the cardiac lead;

advancing the cardiac lead through the guide catheter lumen to position the distal electrode of the cardiac lead at an implantation site, wherein at least a portion of the cardiac lead is maintained within the guide catheter lumen;

providing a wire sheath having a sheath outer diameter dimensioned to be received within the lead body lumen, a lead clamp movable along the length of the wire sheath that can engage with the lead connector element, a sheath lumen, and a sheath hub incorporating a friction element surrounding the sheath lumen;

providing an elongated core wire having a core wire outer diameter sized to be received in the sheath lumen in frictional engagement with the friction element;

inserting the elongated core wire into the sheath lumen to form a lead stabilization and extension wire having an extension wire length corresponding to the length of the wire sheath and the length of the core wire extending outside the sheath lumen, whereby the frictional engagement of the core wire with the friction element maintains the extension wire length;

inserting a distal portion of the extension wire through the proximal lumen opening to extend through a proximal portion of the lead body lumen and to dispose a proximal extension wire length, substantially corresponding to the length of the guide catheter body, outside the lead body lumen;

affixing the lead clamp to the lead connector assembly to maintain the distal portion of the extension wire within the lead body lumen and the proximal extension wire length outside the lead body lumen;

applying stabilization force to the core wire extending proximally from the guide catheter to stabilize the lead body;

retracting the guide catheter over the lead body to dispose the guide catheter body substantially over the proximal extension wire length thereby exposing the lead connector assembly;

detaching the lead clamp from the lead connector assembly; and withdrawing the distal portion of the lead stabilization and extension wire from the lead body lumen through the proximal lumen opening leaving the distal electrode at the implantation site.

27. The method of claim 26, wherein the step of advancing the cardiac lead further comprises:

advancing a stiffening stylet through the proximal lumen opening into the lead body lumen;

inserting and advancing the cardiac lead and stylet through the guide catheter lumen to advance the distal electrode out of the guide catheter lumen and adjacent tissue to be stimulated; and retracting the stylet from the lead body lumen and through the proximal lumen opening.

28. The method of claim 26, further comprising:

advancing a guidewire through the incision and the vasculature until a distal end of the guidewire is located in the coronary vessel and the proximal end of the guidewire is outside the skin incision, and wherein:

the step of advancing the guide catheter comprises advancing the guide catheter over the guidewire; and the step of advancing the cardiac lead comprises:

inserting the proximal end of the guidewire through a distal lumen end opening the lead body lumen;

advancing the lead distally over the guidewire and through the guide catheter lumen to position the distal electrode of the cardiac lead at an implantation site; and retracting the guidewire from the lead body lumen.

* * * * *

UNITED STATES PATENT AND TRADEMARK OFFICE
CERTIFICATE OF CORRECTION

| | |
|---|---|
| PATENT NO. | : 7,283,878 B2 |
| APPLICATION NO. | : 10/963184 |
| DATED | : October 16, 2007 |
| INVENTOR(S) | : Thomas D. Brostrom, Ryan T. Bauer and Douglas S. Hine |

It is certified that error appears in the above-identified patent and that said Letters Patent is hereby corrected as shown below:

Claim 14, Col. 16, line 5, delete "a faction element" and insert in place thereof
-- a friction element --

Signed and Sealed this

Third Day of February, 2009

JOHN DOLL
*Acting Director of the United States Patent and Trademark Office*